(12) United States Patent
    Bäck

(10) Patent No.: US 10,786,399 B2
(45) Date of Patent: Sep. 29, 2020

(54) DISPOSABLE PANT-TYPE ABSORBENT ARTICLE

(71) Applicant: SCA Hygiene Products AB, Gothenburg (SE)

(72) Inventor: Lucas Bäck, Gothenburg (SE)

(73) Assignee: Essity Hygiene and Health Aktiebolag, Gothenburg (SE)

(*) Notice: Subject to any disclaimer, the term of this patent is extended or adjusted under 35 U.S.C. 154(b) by 411 days.

(21) Appl. No.: 15/758,612

(22) PCT Filed: Sep. 29, 2015

(86) PCT No.: PCT/SE2015/051032
§ 371 (c)(1),
(2) Date: Mar. 8, 2018

(87) PCT Pub. No.: WO2017/058069
PCT Pub. Date: Apr. 6, 2017

(65) Prior Publication Data
US 2018/0303681 A1      Oct. 25, 2018

(51) Int. Cl.
*A61F 13/15*      (2006.01)
*A61F 13/491*    (2006.01)
(Continued)

(52) U.S. Cl.
CPC .... *A61F 13/4915* (2013.01); *A61F 13/15804* (2013.01); *A61F 13/49011* (2013.01);
(Continued)

(58) Field of Classification Search
CPC ............ A61F 13/4915; A61F 13/59011; A61F 13/534; A61F 13/494; A61F 13/49009;
(Continued)

(56) References Cited

U.S. PATENT DOCUMENTS 5,391,588 A    2/1995   Sakamoto et al.
6,179,820 B1   1/2001   Fernfors
(Continued)

FOREIGN PATENT DOCUMENTS

CN    1364452 A     8/2002
CN    101909560 A   12/2010
(Continued)

OTHER PUBLICATIONS

Office Action (Written Opinion) dated Mar. 14, 2020, by the Brazilian Patent Office in corresponding Brazilian Patent Application No. BR112018006124, and an English Translation of the Office Action. (6 pages).

(Continued)

*Primary Examiner* — Jacqueline F Stephens
(74) *Attorney, Agent, or Firm* — Buchanan Ingersoll & Rooney PC

(57) ABSTRACT

A disposable pant-type absorbent article adapted for a male user. The disposable pant-type absorbent article includes a chassis having a front section and a back section, an absorbent core, a front region configured for receiving the genitals of a male user, in which the front section at least partly is made of an elastic material comprising at least one elastic element. The absorbent core within a front region, under the influence of side elastic elements and elastic web material is adapted to bulge outwardly during use of the article to form a bowl shaped portion for receiving the genitals of a male user.

26 Claims, 8 Drawing Sheets

(51) Int. Cl.
*A61F 13/49* (2006.01)
*A61F 13/534* (2006.01)
*A61F 13/494* (2006.01)
*A61F 13/53* (2006.01)

(52) U.S. Cl.
CPC .......... *A61F 13/534* (2013.01); *A61F 13/494* (2013.01); *A61F 2013/530481* (2013.01)

(58) Field of Classification Search
CPC .......... A61F 13/49011; A61F 13/49014; A61F 13/49019; A61F 13/4902; A61F 2013/530481; A61F 2013/4948; A61F 2013/530883; A61F 2013/49025; A61F 2013/49026; A61F 2013/49028; A61F 2013/49031; A61F 2013/49033; A61F 2013/49034; A61F 2013/49039; A61F 2013/49038
USPC .............. 604/349, 347, 346, 385.24, 385.23, 604/385.25, 385.26, 385.27, 385.29, 604/385.3
See application file for complete search history.

(56) References Cited

U.S. PATENT DOCUMENTS

| | | | |
|---|---|---|---|
| 2002/0068919 A1 | 6/2002 | Kawakami et al. | |
| 2003/0023224 A1 | 1/2003 | Ishikawa et al. | |
| 2005/0137563 A1 | 6/2005 | Van Gompel et al. | |
| 2008/0269711 A1* | 10/2008 | Sasayama et al. ...... | A61F 13/15 604/385.09 |
| 2010/0076394 A1 | 3/2010 | Hayase et al. | |
| 2011/0015603 A1* | 1/2011 | Sukegawa ..................... | 604/349 |
| 2011/0022019 A1 | 1/2011 | Shimada et al. | |
| 2012/0095430 A1* | 4/2012 | Nakaoka et al. ....... | A61F 13/49 604/349 |
| 2013/0041340 A1 | 2/2013 | Kawakami et al. | |
| 2015/0328056 A1 | 11/2015 | Een et al. | |
| 2015/0328063 A1 | 11/2015 | Esping Östlin et al. | |

FOREIGN PATENT DOCUMENTS

| | | |
|---|---|---|
| CN | 102138844 A | 8/2011 |
| CN | 102905665 A | 1/2013 |
| CN | 203647581 U | 6/2014 |
| CN | 104080427 A | 10/2014 |
| EP | 1 208 825 A2 | 5/2002 |
| EP | 1281379 A2 | 2/2003 |
| EP | 2 221 031 A1 | 8/2010 |
| EP | 2540269 A1 | 1/2013 |
| EP | 2 572 689 A1 | 3/2013 |
| EP | 2786731 A1 | 10/2014 |
| JP | H06179820 A | 6/1994 |
| JP | 2003038554 | 2/2003 |
| JP | 2004261331 | 9/2004 |
| JP | 2006181172 A | 7/2006 |
| JP | 2007097644 | 4/2007 |
| JP | 2011062257 | 3/2011 |
| JP | 2013183938 | 9/2013 |
| JP | 2014144380 A | 8/2014 |
| JP | 2015071007 | 4/2015 |
| RU | 20100146691 | 5/2012 |
| WO | 9634588 A1 | 11/1996 |
| WO | WO 96/34588 A1 | 11/1996 |
| WO | WO 2014/098683 A1 | 6/2014 |
| WO | 2016010617 A1 | 1/2016 |

OTHER PUBLICATIONS

Decision to Grant issued in corresponding Russian Patent Application No. 2018114627/12(022888), dated Feb. 12, 2019 (24 pages).
The extended European Search Report dated May 26, 2020, by the European Patent Office in corresponding European Application No. 20158778.9. (6 pages).
The extended European Search Report dated Feb. 15, 2019, by the European Patent Office in corresponding European Application No. 15905524.3. (8 pages).
Office Action dated Sep. 9, 2019, by the Colombian Patent Office in corresponding Colombian Patent Application No. NC20180003067. (7 pages).
Office Action issued in corresponding European Patent Application No. 15905524.3, dated Sep. 13, 2019 (3 pages).
Office Action issued in corresponding Japanese Patent Application No. 2018516468, dated Jul. 17, 2019, with Engiish Translation (28 pages).
International Search Report (PCT/ISA/210) dated May 31, 2016, by the Swedish Patent Office as the International Searching Authority for International Application No. PCT/SE2015/051032.
Written Opinion (PCT/ISA/237) dated May 31, 2016, by the Swedish Patent Office as International Searching Authority for International Application No. PCT/SE2015/051032.
Office Action (Examination Report No. 1) dated Jun. 14, 2018, by the Australian Patent Office in corresponding Australian Patent Application No. 2015410598. (5 pages).
Office Action issued in corresponding European Patent Application No. 15905524.3, dated Apr. 9, 2019 (4 pages).
Office Action (Notification of the First Office Action) dated May 19, 2020, by the Chinese Patent Office in corresponding Chinese Patent Application No. 201580083485.8, and an English Translation of the Office Action. (30 pages).
Office Action (Notice of Reasons for Rejection) dated May 27, 2020, by the Japanese Patent Office in corresponding Japanese Patent Application No. 2018-516468, and an English Translation of the Office Action. (19 pages).

\* cited by examiner

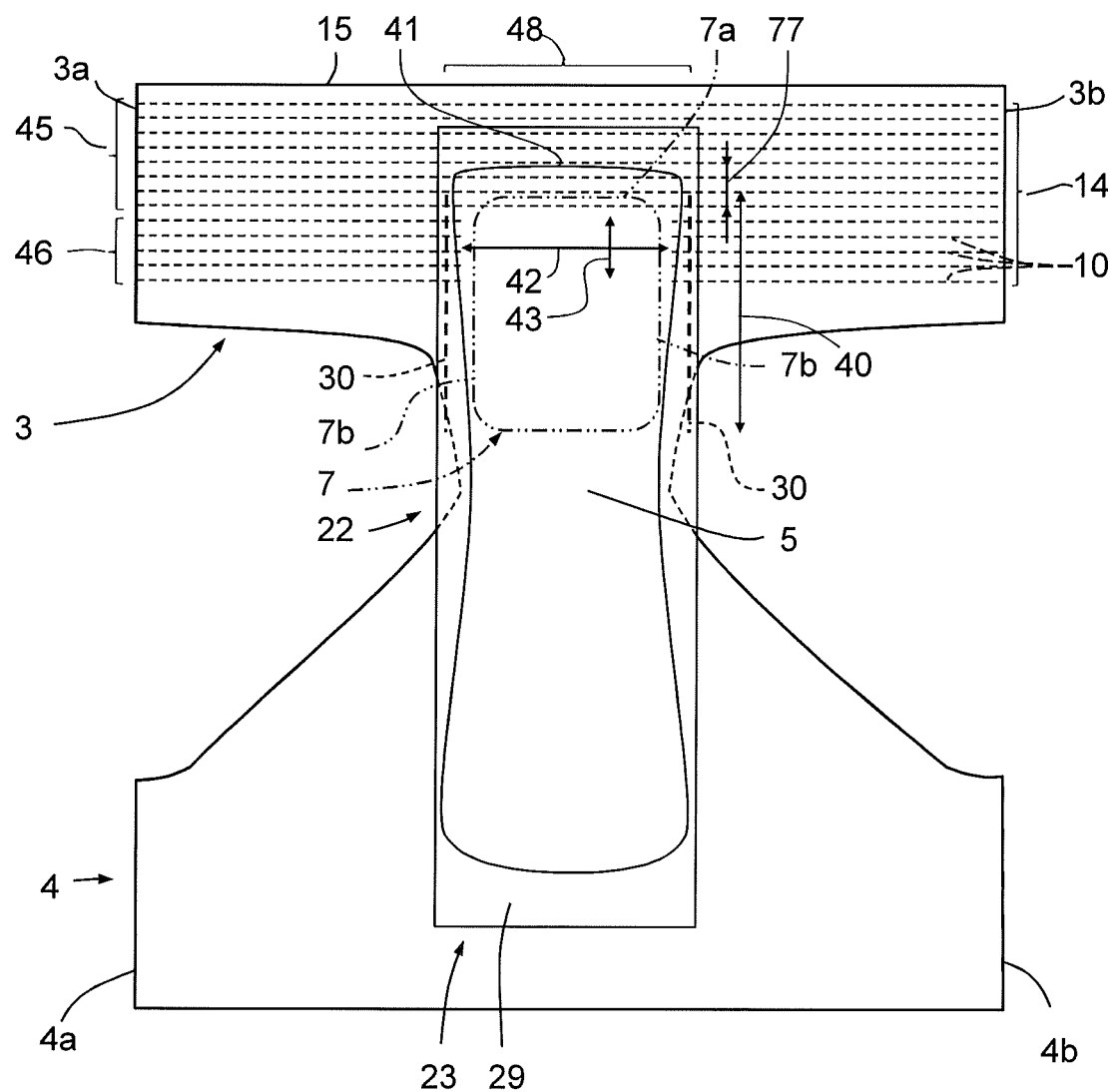
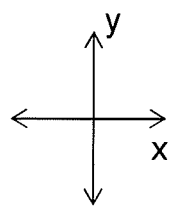
FIG.2

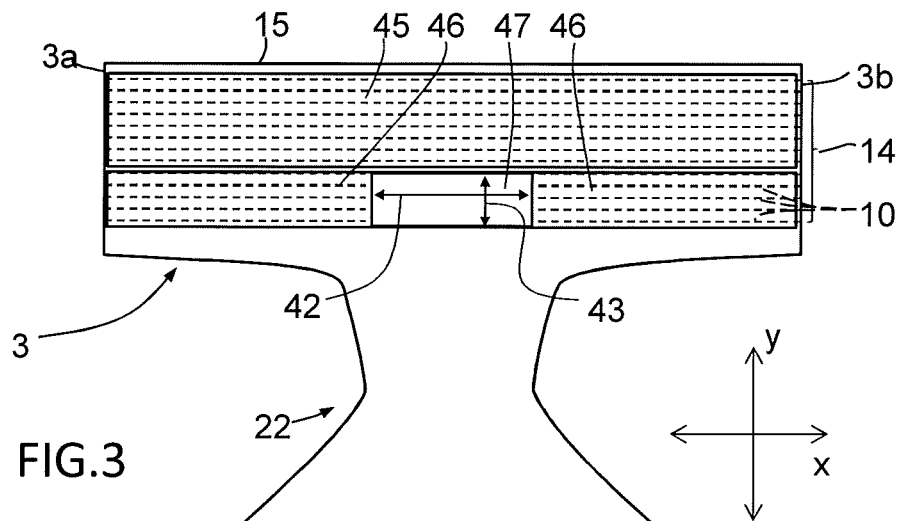
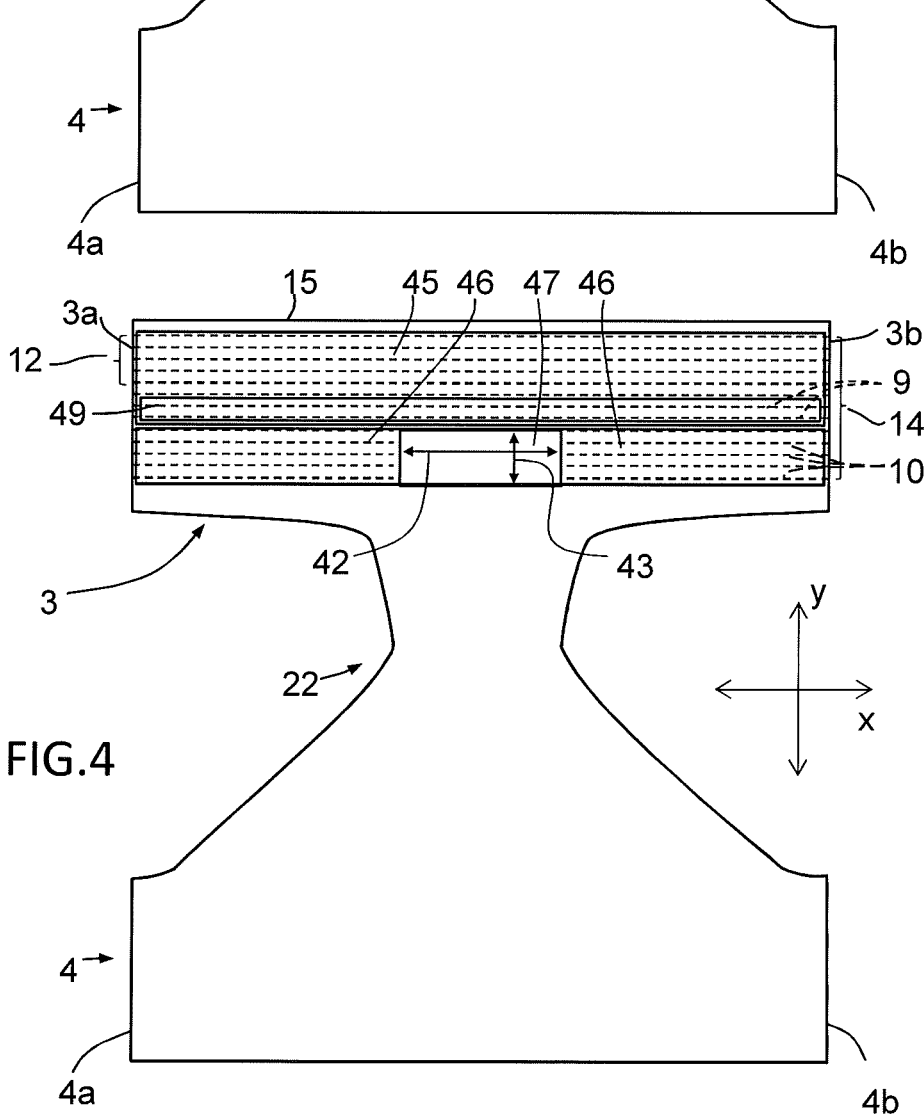

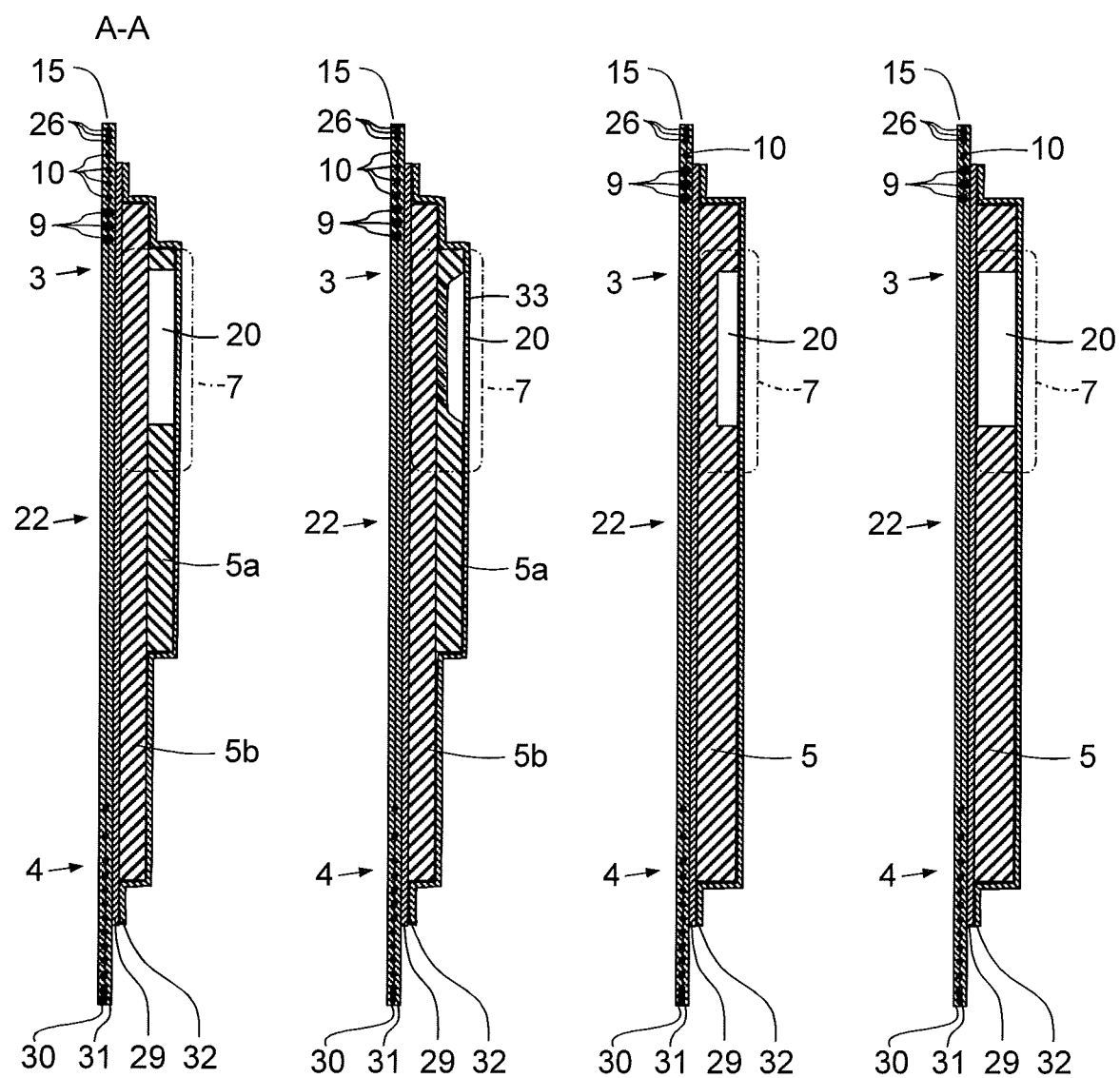

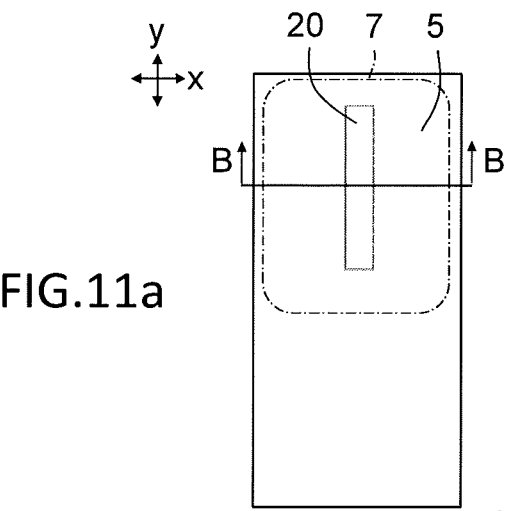
FIG.11a
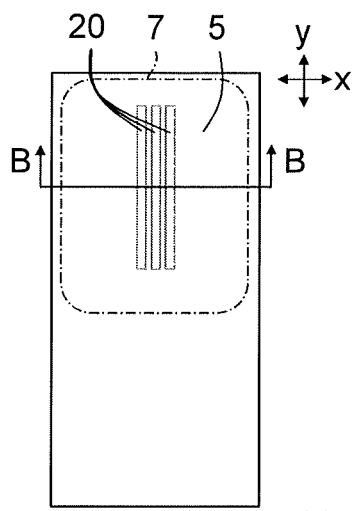
FIG.12a
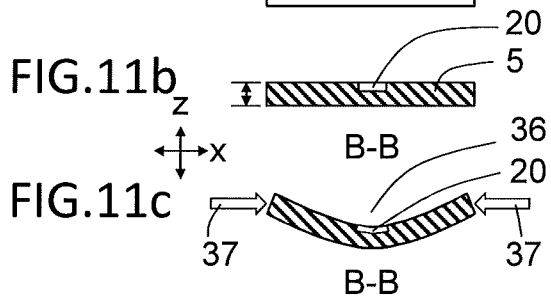
FIG.11b
FIG.11c
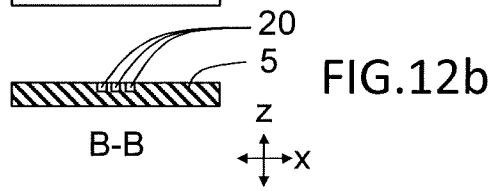
FIG.12b
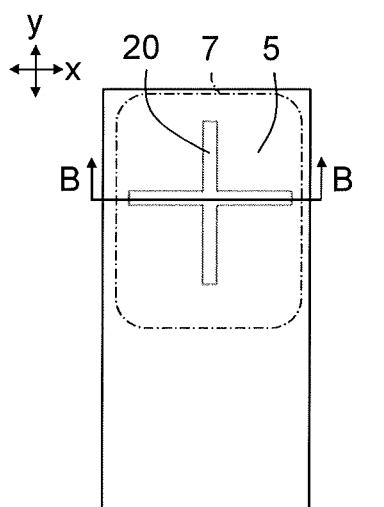
FIG.13a
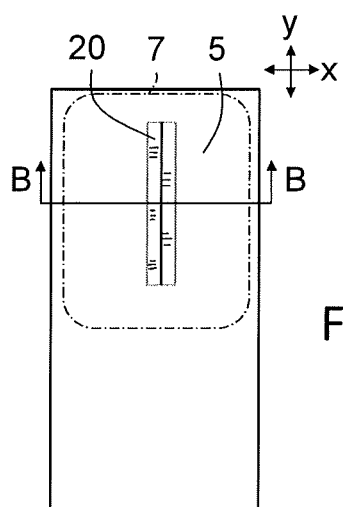
FIG.14a
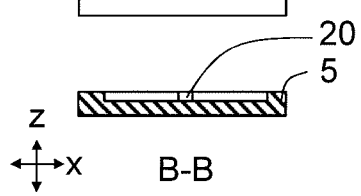
FIG.13b
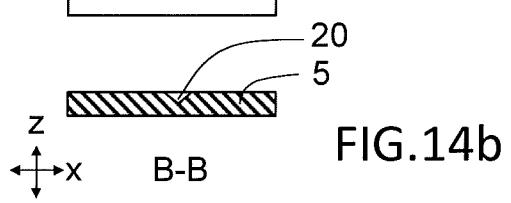
FIG.14b

DISPOSABLE PANT-TYPE ABSORBENT ARTICLE

TECHNICAL FIELD

This disclosure relates to a disposable pant-type absorbent article such as a pant diaper, a sanitary pant or incontinence pant specially adapted for a male user, wherein the article comprises a chassis having a front section and a back section and an absorbent core. The disclosure also relates to a method of manufacturing such a disposable pant-type absorbent article.

BACKGROUND

There is general desire in the field of disposable pant-type absorbent articles to provide articles with increased comfort and leakage protection. An approach for accomplishing a more comfortable and leakage secure absorbent article is to adapt the article to the anatomy of the user. Disposable pant-type absorbent articles specifically designed to fit the anatomy of a male user are already known from for example document WO 96/34588.

While the known disposable pant-type absorbent article is satisfactory for its intended use, such a disposable pant-type absorbent article is nonetheless susceptible to improvement relating to wearing comfort and leakage protection.

SUMMARY

An object of the present disclosure is to provide a disposable pant-type absorbent article and associated method for manufacturing the disposable pant-type absorbent article where the previously mentioned problem is at least partly avoided. This object is achieved by the features of the independent claims.

The disclosure concerns a disposable pant-type absorbent article such as a pant diaper, a sanitary pant or incontinence pant specially adapted for a male user, said disposable pant-type absorbent article comprises, a chassis having a front section and a back section, an absorbent core, a front region configured for receiving the genitals of a male user, a longitudinal direction (y) and a transverse direction (x), in which the front section at least partly is made of an elastic material comprising at least one elastic element, wherein a first portion of the elastic material extends over at least a central portion of the absorbent article for pressing a front portion of the absorbent core towards a user during use of the absorbent article, wherein a second portion of an elastic material is located more towards a back than the first portion and includes at least one elongated side elastic element extending along the transverse sides of at least part of the front region, wherein the absorbent article further comprises at least one elongated side elastic element attached in a substantially longitudinal direction on each transverse side of the front region for providing a side gathering effect along the transverse sides of the front region, such that the absorbent core within the front region, under the influence of the elongated side elastic elements and the first portion of the elastic material, is adapted to bulge outwardly during use of the article to form a bowl shaped portion for receiving the genitals of a male user.

It is desirable to provide the disposable pant-type absorbent article with some kind of bowl shaped portion in a front region of the absorbent article configured to receive the genitals of a male user. Such a bowl shaped portion may be deemed as providing an improved comfort to a user when worn because the absorbent article is more adapted to the anatomy of a male user. The bowl shaped portion also may result in improved leakage protection because the side edges of the absorbent core may better adapt to the skin contour of user, such that the side edges of the absorbent core may exhibit improved sealing contact against the skin of a user. A bowl shaped portion may also result in improved leakage protection because any escape of urine may be better confined within the bowl shaped portion, such that a more controlled and predictable flow characteristics may obtained.

The combination of features of the independent claims simplifies forming of a bowl shaped portion in the front region of the disposable pant-type absorbent article. The first portion of the elastic element functions as a barrier of the bowl shaped portion towards the front waist edge by pressing a front portion of the absorbent core towards a user during use of the absorbent article. The first portion of the elastic element may also provide a certain gathering effect of the chassis and absorbent core along a side of the bowl shaped portion facing the front waist edge, thereby assisting forming of the desired outwardly bulging part of the absorbent article in the front region.

The second portion of an elastic material which are located more towards a back than the first portion enables the absorbent core in the front region to bulge outwardly during use of the article, because at least one of the second portion of the elastic material does not extend completely over the front region, i.e. there is certain portion of the front region lacks an elastic element pressing the absorbent core towards the user. This portion lacking elastic element consequently enables the absorbent core to expand outwards in this portion thereby forming a bowl shaped portion.

Finally, the absorbent article further comprises at least one elongated side elastic element attached in a substantially longitudinal direction on each transverse side of the front region for providing a side gathering effect along the transverse sides of the front region. The gathering effect along the sides of the front region serves to contract the absorbent core in the front region in the longitudinal direction, such that absorbent core in the front region bulges outwardly and forms a bowl shaped portion. The gathering effect thus also form lateral side barriers of the bowl shaped portion along the elongated side elastic elements.

Consequently, the combination of features of the independent claims is adapted to form a bowl shaped portion in the absorbent article for receiving the genitals of a male user. This applies to the corresponding method for manufacturing the disposable pant-type absorbent article.

Further advantages are achieved by implementing one or several of the features of the dependent claims.

According to an example embodiment of the absorbent article the elongated side elastic element extends along the core sides towards the crest of the core in the front section and ends in the region between 70 mm below the crest of the core and 20 mm above the crest of core, preferably between 50 mm below the crest of the core and 20 mm above the crest of the core.

According to an example embodiment of the absorbent article, the first portion of the elastic material includes at least one elastic element extending over substantially the entire front section of the chassis. This aspect enables use of a cost-effective manufacturing process when manufacturing the elastic laminated web material.

According to a further example embodiment of the absorbent article, at least one first portion of an elastic element is located either between the absorbent core and a waist elastic region, or between a thickest portion of the absorbent core and a front edge of the absorbent core, or up to a distance of 50 millimetres further down towards the back section as measured from the front edge of the absorbent core. These alternative locations of the at least one elastic element of the first portion are deemed to provide satisfactory results in terms of forming of the side barrier of the bowl shaped portion towards the front waist edge.

According to a further example embodiment of the absorbent article, the first portion of the plurality of elastic elements includes a high tension zone compared with a longitudinally offset neighbouring region of the first portion of the plurality of elastic elements, wherein the high tension zone is located closer to the back section than the a longitudinally offset neighbouring region of the first portion. A high tension zone further improves forming of the side barrier of the bowl shaped portion towards the front waist edge. A high tension zone may also result in a stronger gathering effect along the front waist edge side of the front region, thereby generating a contraction force on the chassis and absorbent core in the transverse direction, thereby assisting the shaping of the absorbent core into an outwards bulging shape with a bowl shaped portion.

According to a further example embodiment of the absorbent article, all elastic elements in the high tension zone have a higher elastic force than elastic elements in a longitudinally offset neighbouring region of the first portion. A focused and limited high tension zone is deemed cost-effective.

According to a further example embodiment of the absorbent article, the high tension zone comprises 1 to 5 elastic threads, specifically 2 to 4 elastic threads. This number of threads is deemed satisfactory in view of increased tension and manufacturing cost.

According to a further example embodiment of the absorbent article, the high tension zone is located along a front section of the front region. The front section of the front region may be deemed the desired location for the front waist edge side of the bowl shaped portion.

According to a further example embodiment of the absorbent article, the high tension zone comprises at least one individual elastic elements having a higher modulus of elasticity than a neighbouring elastic element; and/or at least one individual elastic element having a stronger pretension than a neighbouring elastic element; and/or a set of individual elastic threads having a smaller longitudinal separation from each other than a set of neighbouring elastic threads.

According to a further example embodiment of the absorbent article, the at least one elastic thread of the high tension zone element is located either between the absorbent core and a waist elastic region, or between a thickest portion of the absorbent core and a front edge of the absorbent core, or up to a distance of 50 millimetres further down towards the back section as measured from the front edge of the absorbent core. These alternative locations of the at least one elastic thread of the high tension zone are deemed to provide satisfactory results in terms of forming of the side barrier of the bowl shaped portion towards the front waist edge.

According to a further example embodiment of the absorbent article, a ratio of total mass of absorption material between the front half of the absorbent core and the back half of the absorbent core in a longitudinal direction is at least 60/40, specifically 70/30, and more specifically 80/20. The absorbent article is specially adapted for a male user and therefore a substantial portion of the absorbent mass is better used when applied at the front half of the absorbent core.

According to a further example embodiment of the absorbent article, the absorbent core comprises at least one weakening feature within the front region for reducing bending stiffness of the absorbent core within the front region. A weakening feature within the absorbent core simplifies bulging outward shaping of the absorbent core, such that the desired bowl shaped portion may more easily be accomplished.

According to a further example embodiment of the absorbent article, weakening feature has an elongated extension arranged substantially in the longitudinal direction of the article for simplifying folding of the absorbent core around a fold line extending substantially in the longitudinal direction. This arrangement is deemed providing a simplified forming of the bowl shaped portion. The term substantially in the longitudinal direction of the article herein refers to about +/−40 degrees around the longitudinal direction, specifically +/−25 degrees around the longitudinal direction, and more specifically +/−10 degrees around the longitudinal direction.

According to a further example embodiment of the absorbent article, weakening feature has a longitudinal extension of about 5 to 20 centimetres, specifically about 7 to 17 centimetres, and more specifically about 9 to 15 centimetres, as measured in an extended state of the absorbent core. These dimensions are deemed suitable for accomplishing the desired bowl shaped portion.

According to a further example embodiment of the absorbent article, a distance from a centre of the weakening feature to a waist edge of the front section in the longitudinal direction is about 5 to 35 centimetres, specifically about 10 to 30 centimetres, and more specifically about 15 to 25 centimetres, as measured in an extended state of the absorbent core and chassis. These dimensions are deemed suitable for accomplishing the desired bowl shaped portion.

According to a further example embodiment of the absorbent article, weakening feature of the absorbent core comprises one or more elongated slits, channels, or compressions within the absorbent core, or a set of discrete slits, channels or compressions arranged along a substantially straight line within the absorbent core. These alternatives are deemed suitable for accomplishing the desired bowl shaped portion.

According to a further example embodiment of the absorbent article, the absorbent core, as seen in a thickness direction of the core, comprises an inner region that is adapted to face a user and an outer region that is adapted to face the garment of user, and the weakening feature is located in the inner region of the absorbent core. Having the weakening in the inner region enables simplified forming of an outwardly convex and internally concave shape, which is suitable for forming the bowl shaped portion.

According to a further example embodiment of the absorbent article, the absorbent core comprises at least two layers located on top of each other, and the weakening feature is provided in an inner layer of the two layers. Having the weakening in the inner layer enables simplified forming of an outwardly convex and internally concave shape, which is suitable for forming the bowl shaped portion.

According to a further example embodiment of the absorbent article, the outer layer is free from a weakening feature within the front region. The outer layer thereby has improved absorption capacity.

According to a further example embodiment of the absorbent article, each elongated side elastic element extends backwards in the longitudinal direction along the sides of the absorbent core to form leg elastic members along the periphery of the leg openings in a crotch section of the article. The dual functionality of the side elastic members as lateral side barriers of the bowl shaped portion and leg elastics in the crotch region simplifies manufacturing of the absorbent article.

According to a further example embodiment of the absorbent article, the web material of the chassis is substantially free from any tensioned elastic threads at a central portion of the front section. This allows satisfactory forming of the bowl shaped portion.

According to a further example embodiment of the absorbent article, the central portion of the front section has a substantially square-shape with an area in the range of 20-150 square centimetres, specifically 50-135 square centimetres, and more specifically 80-120 square centimetres. These dimensions are deemed suitable for forming the bowl shaped portion for various sizes of the absorbent article.

According to a further example embodiment of the absorbent article, the elastic threads of the central portion of the front section has been interrupted and are not attached to any sheet of web material of the laminated elastic web material within the central portion. This approach for forming the central portion free from tensioned elastic elements enables use of a cost-efficient manufacturing process.

According to a further example embodiment of the absorbent article, each of the front and back sections of the chassis comprises a waist edge, a pair of side edges and a pair of leg edges, wherein the front and back sections are joined to each other by means of a pair of side connections, each side connection extending along two opposite side edges to at least partly define a waist-opening and a pair of leg-openings.

Further areas of applicability will become apparent from the description provided herein.

BRIEF DESCRIPTION OF DRAWINGS

In the detailed description below reference is made to the following figure, in which:

FIG. 2 shows a schematic view of the absorbent article of FIG. 1 in a flat configuration, FIG. 3 shows a schematic view of a chassis suitable for the absorbent article of FIG. 1 in a flat configuration, FIG. 4 shows a schematic view of an alternative example embodiment of the chassis in a flat configuration, FIG. 7 shows a cross-section of the example embodiment of the absorbent article of FIG. 5, FIG. 8 shows a cross-section of an alternative example embodiment of the absorbent article according to the disclosure, FIG. 9 shows a cross-section of a further alternative example embodiment of the absorbent article according to the disclosure, FIG. 10 shows a cross-section of still a further alternative example embodiment of the absorbent article according to the disclosure, FIG. 11a-11c shows various views of an example embodiment of the absorbent core according to the disclosure, FIG. 12a-12b shows various views of an alternative example embodiment of the absorbent core according to the disclosure, FIG. 13a-13b shows various views of a further alternative example embodiment of the absorbent core according to the disclosure, FIG. 14a-14b shows various views of still a further alternative example embodiment of the absorbent core according to the disclosure.

DETAILED DESCRIPTION OF EXAMPLE EMBODIMENTS

Various aspects of the disclosure will hereinafter be described in conjunction with the appended drawings to illustrate and not to limit the disclosure, wherein like designations denote like elements, and variations of the described aspects are not restricted to the specifically shown embodiment, but are applicable on other variations of the disclosure.

Figure 1:
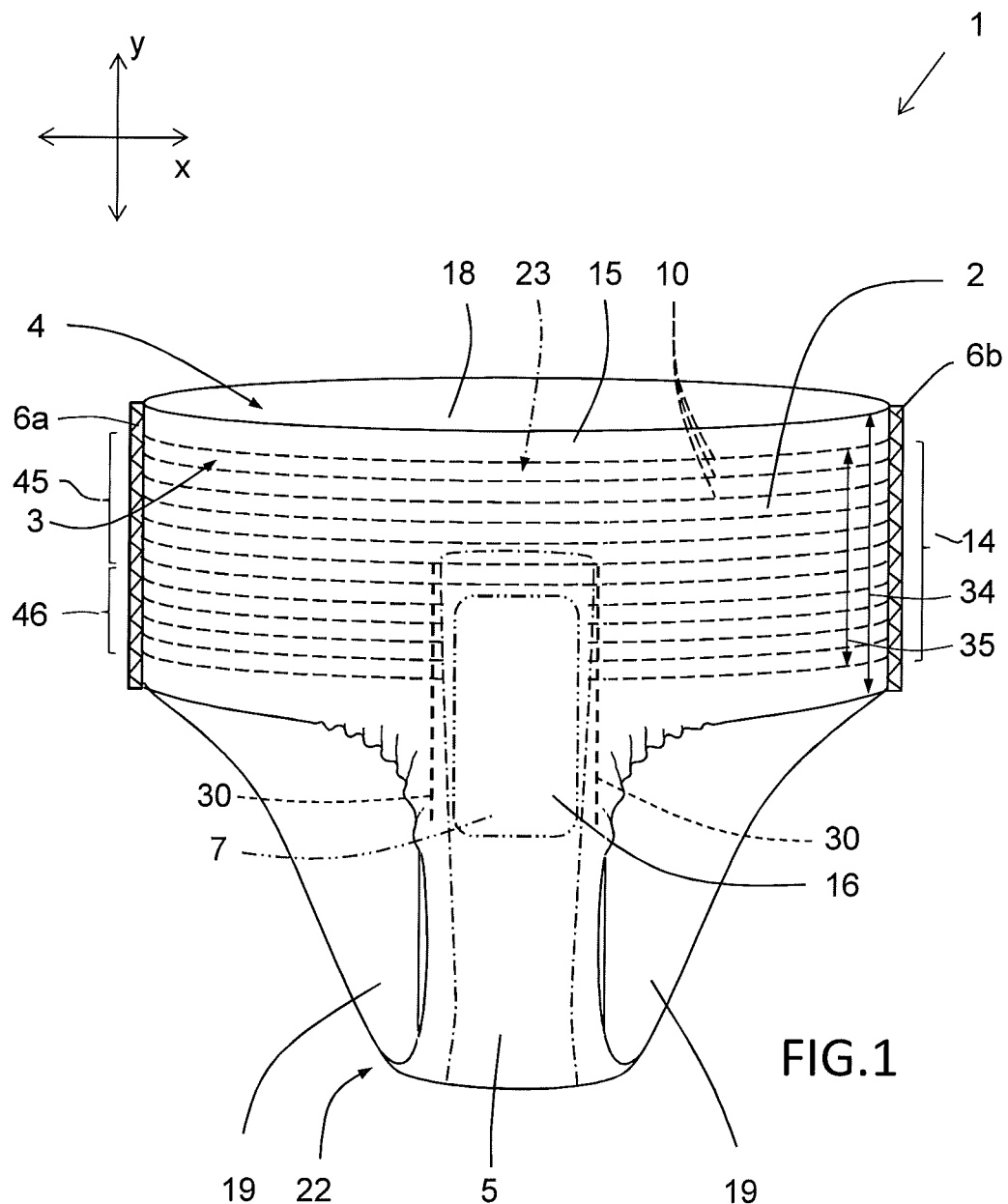
FIG. 1 shows a schematic perspective view of an example embodiment of the absorbent article according to the disclosure.

In FIG. 1 of the drawings an example embodiment of a disposable pant-type absorbent article 1 specially adapted for a male user is schematically illustrated in an assembled and ready-to-use state. The pant-type absorbent article 1 is for example pant diaper, a sanitary pant or an incontinence pant adapted for use of an adult male user. The pant-type absorbent article 1 according to the example embodiment of FIG. 1 comprises a single-piece chassis 2 having a front section 3, a back section 4 and a crotch section 22 connecting the front and back sections 3, 4. The absorbent article 1 further comprises an insert 23 with an absorbent core 5. The insert 23 may be manufactured separately from the chassis 2 and inserted and fastened to the chassis in a suitable manufacturing step. Alternatively, the insert 23 and absorbent core 5 are made integrally with the manufacturing of the chassis. Side edges 3a, 3b of the front section 3 are permanently or re-closably attached to side edges 4a, 4b respectively to form side-connections 6a, 6b of the assembled absorbent article 1, such as to at least partly define a waist-opening 18 and a pair of leg-openings 19. The side-connections 6a, 6b may be made by means of side-seams.

In FIG. 2 of the drawings the same example embodiment of the disposable pant-type absorbent article 1 is schematically illustrated in flat, non-assembled state, and without the side edges 3a, 3b, 4a, 4b attached to each other. The pant-type absorbent article 1 comprises a longitudinal direction y that is substantially parallel with a direction of elongation of the absorbent core, as seen in a flat state before joining the side-connections 6a, 6b, and a transverse direction x that is perpendicular to the longitudinal direction y, and according to the herein shown example embodiment substantially parallel with a front waist edge 15 of the absorbent article 1. Folding of the flat absorbent article 1 in FIG. 2 around a fold line extending in the transverse direction x and joining of the side edges 3a, 3b, 4a, 4b to side-connections 6a, 6b results in the assembled absorbent article of FIG. 1.

The pant-type absorbent article 1 of the example embodiment illustrated in FIG. 1 and FIG. 2 comprises an elastic sheet of web material in at least the front section 3, and preferably also the back section 4. Manufacturing of the elastic web material of the front section 3 is typically performed by feeding a first and a second continuous substantially non-elastic sheet of web material, such as for example a substantially non-elastic nonwoven material, along a machine direction, while simultaneously feeding a plurality of elastic threads arranged parallel with one another. Subsequently, the first and second sheets of web material are joined to each other with a plurality of continuous elastic threads 9, 10 located between the first and second sheets.

The elastic threads are attached to the first and second sheets in a tensioned state, and parallel with, the web material. The elastic threads 10 may for example have adhesive applied to it before being fastened in a tensioned state to the web material. Alternatively, or in combination, the web material itself may have adhesive applied to it for securing the elastic threads 10 thereto. Upon cutting of the laminated elastic web material in a machine cross direction, i.e. a direction perpendicular to the machine direction, individual absorbent article chassis 2 are provided. When the elastic web material of the chassis 3 is no longer held in stretched in the transverse direction x the sandwiched elastic threads 10 will cause the web material to gather, i.e. to contract in the transverse direction x and to form small undulations in the web material. An example manufacturing process for such an elastic web material is described more in detail in document WO2014098683 A1, which is referred to in its entirety.

The front section 3 comprises an elastic belly region 14 having a having a plurality of individual parallel elastic threads 9. The elastic belly region 14 extends over substantially the entire front section 3 in the transverse direction x. The individual parallel elastic threads 9 extend from one side edge 6a to the other side edge 6b. In the disclosed example embodiment of FIG. 1 and FIG. 2 the elastic threads 9 extends parallel with the transverse direction x, but they may alternatively locally exhibit a small inclination with respect to the transverse direction x, such as for example +/−30 degrees around the transverse direction x, specifically +/−20 degrees around the transverse direction x, and more specifically +/−10 degrees around the transverse direction x.

The elastic belly region 14 extends over substantially the entire front section 3 also in the longitudinal direction y. A length 35 of the elastic belly region 14 in the longitudinal direction y, as measured between the two outermost elastic threads 10 of the elastic belly region 14 in the longitudinal direction at a side edge 61, 6b, typically amounts to more than 70% of the length 34 of the chassis in the longitudinal direction at the side edge 6a, 6b, specifically more than 80%, and more specifically more than 90%. In absolute numbers the maximal length 34 of the front section 3 in the longitudinal direction y may be in the range of 5-30 centimetres, specifically in the range of 10-20 centimetres, as measured in an extended state of the absorbent article.

The gap between individual elastic threads may be in the range of 2-10 millimetres, specifically in the range of 3-7 millimetres.

A front region 7 of the pant-type absorbent article 1, as schematically illustrated by a dash-dot-dot line in FIG. 1 and FIG. 2, is configured for receiving the genitals of a male user. For accomplishing a high degree of comfort and leakage protection, the pant-type absorbent article 1 is designed to adapt its shape to the anatomy of a male user. Specifically, the pant-type absorbent article 1 is adapted to bulge outwardly in the front region 7 during use of the article to form a bowl shaped portion for receiving the genitals of a male user. By means of the bowl shaped portion an improved fitting of the pant-type absorbent article 1 is accomplished, such that the user comfort and at least experienced leakage protection is increased.

The bowl shaped portion is adapted to be formed mainly based on three aspects of the absorbent article, namely at least one elastic thread extending continuously over a central portion of the absorbent article for pressing a front portion of the absorbent core towards a user during use of the absorbent article, at least one elastic thread extending on the transverse sides of the front region 7 but not completely over the front region 7 for enabling the absorbent core in the front region to bulge outwardly during use of the article, and one elongated side elastic element attached in a substantially longitudinal direction on each transverse side 7b of the front region 7 for providing a side gathering effect along the transverse sides 7b of the front region 7.

These three aspects jointly contribute to providing an absorbent core within the front region, which absorbent core under the influence of the side elastic elements and the a laminated elastic web material is adapted to bulge outwardly during use of the article to form a bowl shaped portion for receiving the genitals of a male user.

In FIG. 1 and FIG. 2, and also FIG. 3 which has been provided for more clearly illustrating the arrangement of the elastic threads 10 of the front section 3 of FIG. 1 and FIG. 2, a first portion 45 of the plurality of elastic threads includes several elastic threads that are extending continuously over a central portion 48 of the absorbent article in the transverse direction x for pressing a front portion of the absorbent core 5 towards a user during use of the absorbent article. The first portion 45 may for example comprise 2-20 individual threads, more specifically 5-15 threads. The elastic threads of the first portion 45 press the absorbent core 5 towards the user to close the bowl shaped portion towards the front waist edge 15 side.

The elastic threads of the first portion 45 may also provide a certain gathering effect on the material of the chassis and/or absorbent core 5 in the along a front section 7a of the front region 7. The gathering effect of the front section 7a of the front region 7 defines a front boundary of the bowl shaped portion, such that appropriate sealing of the side of the bowl shaped portion facing the front waist edge 15 is accomplished.

The first portion 45 of the plurality of elastic threads does not include any waist elastic feature.

The example absorbent article of FIG. 1 and FIG. 2 further comprises a second portion 46 of the plurality of elastic threads 10 located more towards a back than the first portion 45, wherein the second portion 46 also includes several elastic threads extending on the transverse sides of the front region 7 but not completely over the front region 7 for enabling the absorbent core in the front region to bulge outwardly during use of the article. Each second portion 46 may for example comprise 2-15 individual threads, more specifically 3-10 threads.

For avoiding that the bowl shaped portion is compressed inwardly and reduced in size the tensioned elastic feature crossing the front region 7 is limited. Having an elastic feature located adjacent a side edge 7b of the front region 7 has no negative effect on the forming of the bowl shaped portion, on the contrary, elastic feature along the side edge 7b assist forming of a bowl shaped portion. However, an elastic feature located across the front region 7 may negatively influence the desired outward bulging effect that forms the bowl shaped portion. It may thus be advantageous to have the web material of the chassis 2 substantially free from any tensioned elastic feature at the front region 7.

For accomplishing the desired reduction of elastic feature, in particular reduction of elastic threads 10 of the front section extending in the transverse direction x, a central portion 47 of the front section 3 overlapping the absorbent core 5 may be free from tensioned elastic threads. The central portion 47 of the front section 3 may for example have a substantially square-shape with a length 42 in the transverse direction x of about 5-20 centimetres, specifically 7-17 centimetres, and a length 43 in the longitudinal direction x of about 5-20 centimetres, specifically 7-17 centimetres. The area size of the central portion of the front section 3 may be in the range of 20-150 square centimetres, specifically 50-135 square centimetres, and more specifically 80-120 square centimetres. The central portion 47 of the front section 3 corresponds to the surface area of the absorbent article having elastic threads extending on the transverse sides of the central portion 47 but not over the central portion 47.

In a pant-type absorbent article having a front section 3 with inner and outer sheets of web material attached to each other and with a plurality of individual elastic threads sandwiched there between, the absorbent core typically extends into the area of the elastic threads of the front section 3. Consequently, one solution for avoiding having the elastic threads of the front section 3 extending across the centre of the front region 7 is to have the individual elastic threads 10 of the front section 3 extending from each side edge 6a, 6b towards the front region 7 but being interrupted adjacent the front region 7, such as for example at the border of the insert 23, at the border of the absorbent core 5, or at the border of a specific layer of the absorbent core 5.

Interruption of elastic threads extending in the transverse direction across the front section 3 may for example be performed by first avoiding having the elastic threads being fastened to the chassis in the central portion 47 of the front section 3, such as for example by avoiding application of adhesive on the elastic threads in the central portion 47 of the front section 3. Thereafter, the elastic threads extending across the central portion 47 of the front section 3 may be cut or otherwise severed, such that the threads extending across the central portion 47 of the front section 3 are torn and allowed to snap back towards the second portion 46, which are offset from the central portion 47 of the front section 3 in the transverse direction x.

Moreover, the example absorbent article embodiment if FIG. 1 and FIG. 2 further comprises an elongated side elastic element 30 attached in a substantially longitudinal direction on each transverse side 7b of the front region 7 for providing a side gathering effect along the transverse sides 7b of the front region 7. Each elongated side elastic element 30 may include one or more individual elastic threads, such as for example two, three or four elastic threads placed parallel to each other and with a gap between each other. The length 40 of the side elastic element 30 in the longitudinal direction y may be in the range of 4-20 centimetres, specifically 5-15 centimetres, and more specifically 5-10 centimetres.

The side elastic element 30 may extend from a crotch section 22 towards a front edge 41 of the absorbent core 5. The distance from a front edge 41 of the absorbent core 5 to the edge of the side elastic element 30 may be less than 30 millimetres, and specifically less than 15 millimetres. The side elastic elements 30 may even extend beyond the front edge 41 of the absorbent core 5 towards the front waist edge 15 of the absorbent article 1. The side elastic elements 30 may be attached to the transverse sides of the back sheet 29 of the insert 23, and/or to the transverse sides of the absorbent core 5.

The elongated side elastic elements 30 attached in a substantially longitudinal direction y on each transverse side 7b of the front region 7 are configured for providing a gathering effect along the transverse sides 7b of the front region 7. A gathering effect means that the web material of the chassis and absorbent core 5 within the region of the side elastic element 30 will contract in the direction of extension of the side elastic elements 30. This contraction effect of the material of the absorbent article along the transverse sides 7b of the front region 7 will assist forming of the bowl shaped portion in the absorbent article, and thus generating a more comfortable and leakage secure absorbent article.

Use of a plurality of elastic threads arranged in parallel with one another and extending in a substantially transverse x direction for providing the necessary compressive force for accomplishing a closure of the bowl shaped portion on the side facing the front waist edge 15 is a cost-efficient and manufacturing-friendly approach for achieving a disposable pant-type absorbent article 1 having improved comfort and leakage protection. The application of elastic elements 10 to the front section 3 in a substantially transverse direction x may be realised in a cost-efficient manufacturing process. Moreover, forming a central portion 47 of the front section 3 without elastic threads is also relatively cost-effective approach for providing the bowl shaped portion within the absorbent core.

For accomplishing a high degree of user comfort when wearing the absorbent article substantially the entire front section 3 of the article 1 is made of the elastic web material. However, the normal elastic tension force in the front section 3 may be insufficient for enabling forming of the absorbent core 5 within the front region 7 and for creating an appropriate closure of bowl shaped portion. It may thus be advantageous to provide the first portion 45 of the plurality of elastic threads with a high tension zone 49, as schematically illustrated in FIG. 4. The high tension zone comprises elastic threads 10 having a higher elastic force than elastic threads of a neighbouring region of the first portion. The high tension zone 49 is located closer to the back section 4 than the longitudinally offset neighbouring region of the first portion 45. As a result, the tension in the transverse direction x asserted by the elastic threads in the high tension zone 49 is higher than the tension in the transverse direction x asserted by the elastic web material in a neighbouring region that is longitudinally offset from the high tension zone 49. Hence, by having at least two different degrees of tension in the transverse direction in the front section 3, in particular in the belly region 14 of the front section 3, a high degree of user comfort may be accomplished while still having sufficient tension force for folding the absorbent core 5 within the front region 7 and providing the desired closure of the bowl shaped portion.

The high tension zone 49 is preferably located next to the central portion 47 of the front section 3, on the side of the central portion 47 facing the front waist edge 15. For enabling cost-efficient manufacturing of the absorbent article the high tension zone typically extends from one side edge 3a to the other side edge 3b of the front section 3.

When manufacturing the elastic web material of the front section 3 according to the example process described above the elastic web material will have a plurality of individual elastic threads 10 extending at a separation from and parallel to each other in the transverse direction x. One approach for accomplishing the high tension zone 49 is to use threads 9 having a higher modulus of elasticity in the high tension one 49 compared with threads 10 used in longitudinally offset neighbouring region 12. One may for example replace 1-5, specifically 2-4, and more specifically three conventional elastic threads in the belly region 14 of the front section 3 with threads having a higher modulus of elasticity.

Alternatively, the high tension zone 49 may be accomplished by providing at least one individual elastic thread 9 with a stronger pretension than a neighbouring elastic thread 10. That is, all the threads 10 in the belly region 14 of the front section 3 may have the same modulus of elasticity, but at least one elastic, specifically three elastic threads 9 in the high tension zone 49 are pre-tensioned a higher degree that the elastic threads within the longitudinally offset neighbouring region 12. Since a higher pretension generally means higher tension force according to Hooke's law on strain-stress behaviour of an elastic thread, a high tension zone 49 may be accomplished by using threads with a higher pre-tension.

Still more alternatively, a set of individual elastic threads 9 within the high tension zone 49 may have a smaller separation from each other in the longitudinal direction than a set of neighbouring elastic threads located in a neighbouring region 12. A smaller separation from each other in the longitudinal direction means that more elastic threads are provided per square surface, such that a higher tension in the transverse direction x per square surface is realised.

The high tension zone 49 may alternatively be accomplished by a combination of various alternative solutions described above.

Figure 5:
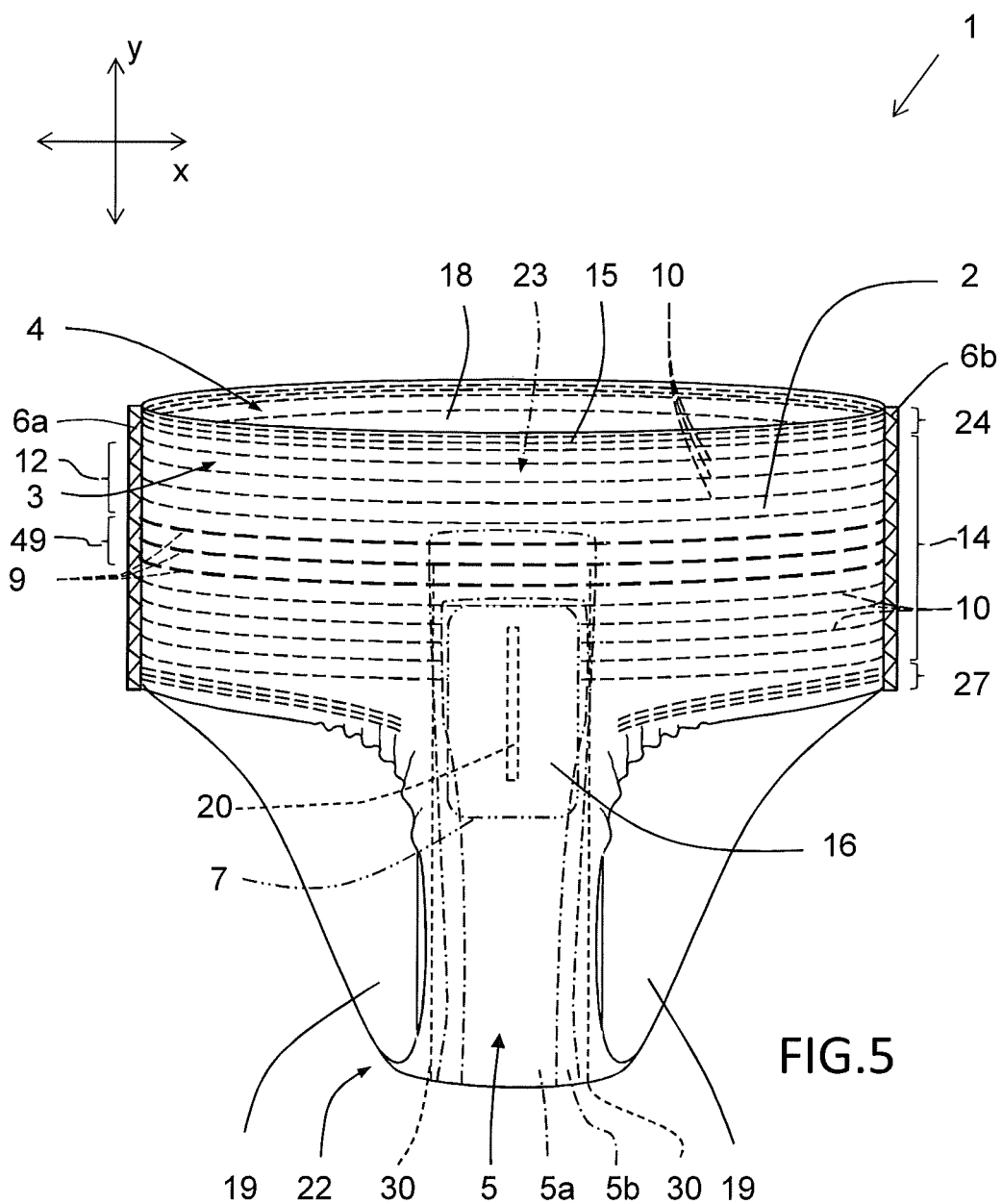
FIG. 5 shows a schematic perspective view of a more detailed example embodiment of the absorbent article according to the disclosure.
Figure 6:
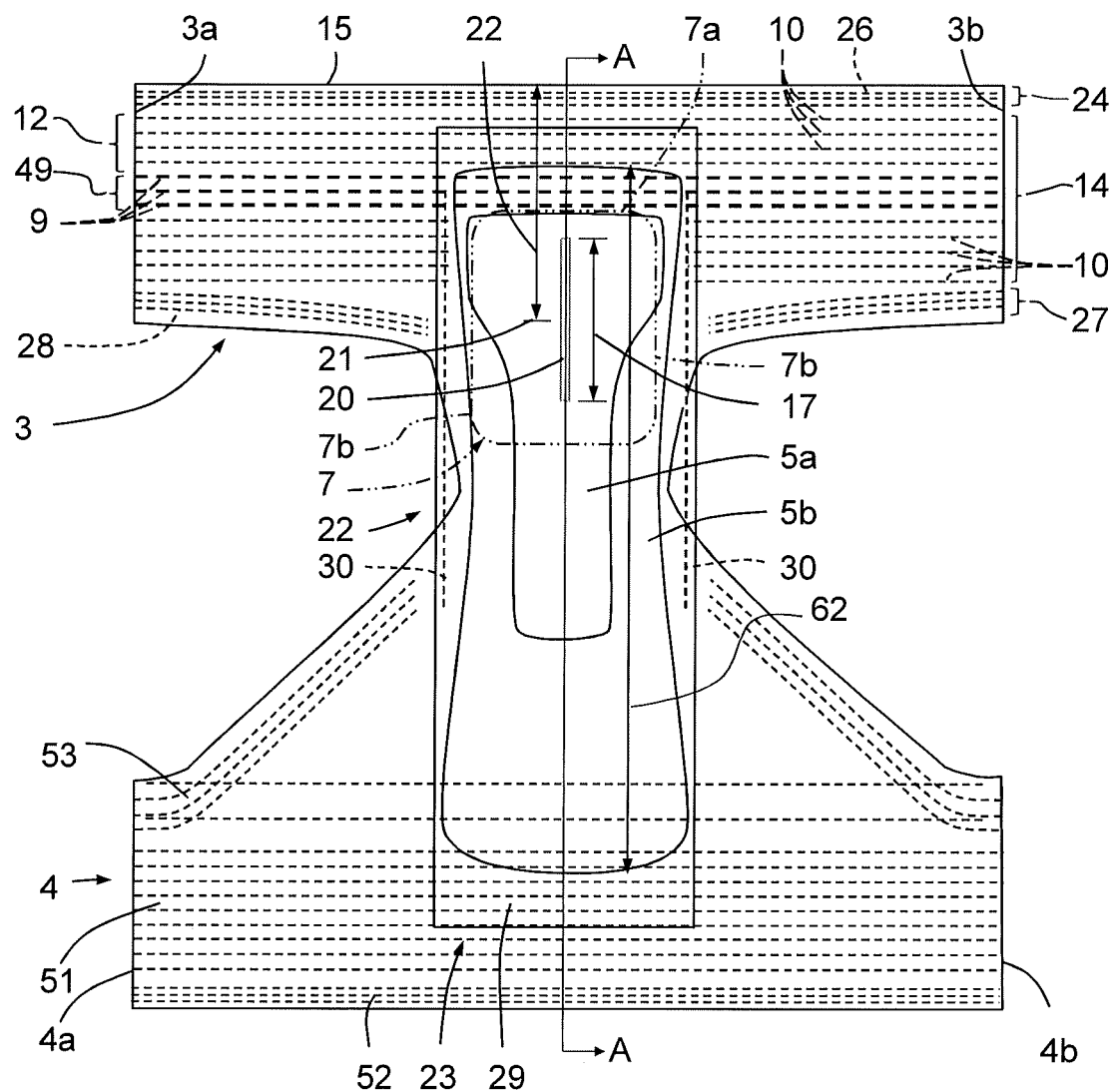
FIG. 6 shows a schematic view of the absorbent article of FIG. 5 in a flat configuration.

The disposable pant-type absorbent article illustrated and described with reference to FIG. 1-4 shows a simplified absorbent article. However, a disposable pant-type absorbent article typically comprises many more features. An example embodiment of a slightly more detailed disclosure of the absorbent article according to the disclosure is shown in FIG. 5 and FIG. 6, wherein FIG. 5 shown the absorbent article in an assembled state and FIG. 6 shown the corresponding absorbent article in a flat state before joining the side edges 3a, 3b, 4a, 4b The example embodiment of FIG. 5 and FIG. 6 comprises an elastic waist region 24 and an elastic leg region 27 located in the front section 3. The elastic waist region 24 has a plurality of individual parallel elastic threads 26, and the elastic leg region 27 has a plurality of individual parallel elastic threads 28.

The elastic belly region 14 is here shown being located between the elastic leg region 27 and elastic leg region 27. The elastic threads 26 of the elastic waist region 24 may be located with a smaller gap from each other compared with the elastic threads 10 of the elastic belly region 14 for obtaining a higher level of tension force in the waist region. The same applies to the threads of the elastic leg region 27.

The absorbent article may further have an elastic back region 51, an elastic waist region 52 at the back section 4 and an elastic leg region 53 at the back section 4.

According to a further example embodiment of the disclosure, each elongated side elastic element 30 may be designed to extend backwards in the longitudinal direction y along the transverse sides of the absorbent core 5 to also form leg elastic members along the periphery of the leg-openings 19 in a crotch section 22 of the article 1. This arrangement thus enables combined use of one-piece longitudinally oriented elastic members 30 on each transverse side of the absorbent core 5, such that the need for mounting of separate leg elastic feature and bowl shaped portion gather elastics can be avoided to save cost and simplify manufacturing. Alternatively, separate elongated side elastic elements may be used for accomplishing a desired gathering effect along the periphery of the leg-openings 19 in a crotch section 22 of the article 1. The elongated side elastic element 30 may be composed of a suitable number of elastic threads positioned parallel and with a gap between each other.

According to yet a further alternative embodiment illustrated in FIG. 5 and FIG. 6, the absorbent core 5 made be made as a laminated product comprising an inner layer 5a and an outer layer 5b. The laminated absorbent core 5 may be secured to a back sheet 29 of web material to form the insert 23. Since the inner and outer layers 5a, 5b in FIG. 5 and FIG. 6 have different sizes the resulting absorbent core 5 has a having varying thickness across the length of the absorbent core 5. In such case, the elastic threads 9 of a high tension zone 49 may be located between a thickest portion of the absorbent core 5 and the front waist edge 15, i.e. across a thinner portion of the absorbent core located in the front region of the absorbent core 5. In the example embodiment of FIG. 1 and FIG. 2, in which the inner layer 5a has a smaller size than the outer layer 5b, the thinner portion of the absorbent core located in the front region of the absorbent core 5 corresponds to an area of the absorbent core having only the outer layer 5b. Alternatively, in case the absorbent core 5 has uniform thickness throughout the longitudinal and transverse extension thereof, the elastic threads 9 of a high tension zone 49 may for example be located between the absorbent core 5 and the front waist edge 15.

The absorbent core 5 may be provided with a design where the front portion has a larger extension in the transverse direction than a rear portion of the absorbent article. This provides an increased absorption capacity in the front region for improved leakage protection when used by a male user.

Moreover, a ratio of mass of absorption material between the front half of the absorbent core 5 and the back half of the absorbent core 5 in a longitudinal direction y is at least 60/40, specifically 70/30, and more specifically 80/20. This means that at least 60% of the total mass of the absorbent core 5 is located in a front half of the absorbent core 5, and only maximal 40% of the total mass of the absorbent core 5 is located in the back half of the absorbent core 5. The front and back half of the absorbent core 5 are herein defined by dividing the total maximal length 62 of the absorbent core 5 in the longitudinal direction in two equally long parts in the longitudinal direction y. Absorbent core is herein defined as being made at least partly from fibrous cellulosic material and/or superabsorbent polymers (SAP).

In cases where the absorbent core 5 is relatively stiff for some reason it may be advantageous to provide the absorbent core 5 with at least one weakening feature 20 within the front region 7 for reducing bending stiffness of the absorbent core 5 within the front region 7. The weakening feature 20 may simplify forming of the bowl shaped portion in the absorbent core 5. In particular, the combination of compressive force applied to the absorbent core 5 in a transverse direction x by means of the elastic threads 10 and reduced bending stiffness of the absorbent core 5 around a fold line extending substantially in the longitudinal direction y may enable simplified forming of the outward bulging of the absorbent core 5 in the front region 7 during use of the absorbent article 1. The weakening feature 20 consequently provides improved creation of a desired bowl-shaped absorbent core 5 in the front region 7. The term bowled-shaped herein refers to an absorbent core having a concave inner surface facing the body of a user, and a convex outer surface 16 facing the garment of a user.

A reduction of bending stiffness of the absorbent core 5 within the front region 7 may according to an example embodiment of the disclosure be accomplished by means of a weakening feature 20 having an elongated extension arranged substantially in the longitudinal direction of the article. A substantially longitudinal extension of the weakening feature 20 enables folding of the absorbent core 5 around substantially longitudinal direction y, such that a suitable bowl shaped portion can be accomplished and configured to fit the anatomy of a male user.

Furthermore, the weakening feature may have a longitudinal extension 17 of about 5 to 20 centimetres, specifically about 7 to 17 centimetres, and more specifically about 9 to 15 centimetres, as measured in an extended state of the absorbent core, and illustrated more in detail in FIG. 5 and FIG. 6. This level of longitudinal extension 17 of the weakening feature corresponds generally to a suitable length for accomplishing a bowl shaped portion rendering a male user the desired high degree of comfort and leakage protection.

A distance from a centre 21 of the weakening feature 20 to the front waist edge 15 in the longitudinal direction may be selected to be about 5 to 35 centimetres, specifically about 10 to 30 centimetres, and more specifically about 15 to 25 centimetres, as measured in an extended state of the absorbent core and chassis. This location of the weakening feature 20 in relation to the front waist edge 15 corresponds generally to a suitable location for accomplishing a bowl shaped portion rendering a male user the desired high degree of comfort and leakage protection.

According to the example embodiment disclosed in FIG. 5 and FIG. 6 the weakening feature 20 comprises a single elongated channel extending in the longitudinal direction y and position in the centre of the absorbent core 5 in the transverse direction x. However, many alternative configurations of the weakening feature are possible within the scope of the present disclosure for accomplishing the desired reduction in bending stiffness of the absorbent core. For example the weakening feature 20 may comprise one or more elongated slits, channels, or compressions within the absorbent core, and/or a set of discrete slits, channels or compressions arranged along a substantially straight line within the absorbent core.

Although many aspects and features have been disclosed in combination in FIG. 5 and FIG. 6, such as having the elongated side elastic element 30 extending backwards to also form leg elastic members along the periphery of the leg-openings 19 in a crotch section 22, or having a laminated absorbent core 5 comprising an inner layer 5a and an outer layer 5b, or providing the absorbent core 5 with at least one weakening feature 20, or providing high tension zone 49 in the front section 3, or having an elastic back region 51, all these aspects may be adopted individually or in any combination with each other. The example embodiment of according to FIG. 5 and FIG. 6 should thus not be viewed and understood as single embodiment merely because a single illustration is provided, but instead as many alternative example embodiments of the absorbent article.

FIG. 7 illustrates schematically a cross-section along cut A-A of FIG. 6. This illustration shows the laminated structure of the absorbent core 5 having an inner layer 5a arranged to face the user, an outer layer 5b arranged further away from the user, and a back sheet 29 of web material. The weakening feature is here designed as a channel extending completely through the inner layer 5a.

The inner layer 5a here thus corresponds to a an inner region of the absorbent core that is adapted to face the user, as seen in a thickness direction of the core, and the outer layer 5b here corresponds to an outer region that is adapted to face the garment of user, and the weakening feature 20 is located in the inner region of the absorbent core 5.

The outer layer may be free from a weakening feature 20 within the front region 7 for providing sufficient absorption capacity within the front region 7.

Also the chassis 2 is illustrated in FIG. 7 with an outer sheet of web material 30, an inner sheet of web material 31, and elastic threads 9, 10, 26 sandwiched there between. The three outermost elastic threads 26 form the waist elastic of the front section 3, the neighbouring four elastic threads 10 form part of the elastic belly region 14, and the following three elastic threads 9 form the high tension zone 49. No further elastic threads are shown in the elastic belly region because they are interrupted at the border to the absorbent core and therefore not included in the cross-section of FIG. 7.

The outer and inner sheets of web material 30, 31 are shown extending across the entire length of the absorbent article in the longitudinal direction y, but one of an outer and inner sheets of web material 30 may alternatively extend only over the front and/or back section 3, 4, and being discontinued over the crotch section 22 since the laminated chassis is mainly useful in areas having an elastic feature attached thereto.

In FIG. 7 a top sheet 32 of web material is also shown extending over the absorbent core on the side facing the user. This top sheet 32 is a liquid pervious that may serve to provide a pleasant skin-contact with the absorbent article, as well as to keep the integrity of the insert 23. The back sheet 29 of web material is preferably made of a liquid impervious material.

FIG. 8 illustrates schematically a cross-section of an alternative design of the absorbent article 1. In the example embodiment the inner layer 5a of the absorbent core 5 comprises a weakening feature 20 in form of a longitudinally extending compression. This may for example be provided by pressing a tool against the outer layer 5a before laminating the outer layer 5a to the inner layer 5b. The material 33 of the outer layer 5a that has been compressed typically exhibits a reduced absorption capacity. Hence, in the example embodiment of FIG. 8 the weakening feature does not extend completely through the inner layer 5a. Otherwise, the design of the absorbent article corresponds to that described with reference to FIG. 7.

In FIG. 9 yet an example embodiment of the absorbent article is illustrated. FIG. 9 schematically shows a cross-section of an alternative design of the absorbent article 1 having a single layered absorbent core 5. The single absorbent core may be divided into an inner region and an outer region, and in the disclosed example embodiment the weakening feature 20 is located merely in the inner region of the absorbent core 5. The weakening feature 20 may for example be a channel, a slit or a compression. As a result of the single layered absorbent core the three elastic threads 9 forming the elongated front elastic element are here displaced towards the front waist edge 15 for simplifying gathering of the front section of the front region 7. Otherwise, the design of the absorbent article corresponds generally to that described with reference to FIG. 7 and FIG. 8.

In FIG. 10 yet an example embodiment of the absorbent article is illustrated. FIG. 10 schematically shows a cross-section of an alternative design of the absorbent article 1 having a single layered absorbent core 5. The single layer absorbent core 5 here comprises a weakening feature 20 that extends completely through the entire absorbent core 5. The weakening feature 20 may for example be a channel or a slit. Other aspects of this embodiment correspond generally to that described with reference to FIG. 9.

Various alternative example embodiments of the absorbent core are disclosed with reference to FIGS. 11a, 12a, 13a and 14a. These example embodiments are all disclosed as a single-layered cored but these examples are equally applicable on multi-layered absorbent cores, as the absorbent core disclosed in FIGS. 7 and 8. The alternative designs of the absorbent core of FIGS. 11a, 12a, 13a and 14a are not intended as exclusive but merely some example embodiments of how the weakening feature 20 according to the disclosure may be implement in an absorbent core.

In FIG. 11a the weakening feature 20 is embodied as a longitudinally extending channel located in the front region 7. In a cross-sectional cut along line B-B is schematically illustrated in FIG. 11b it is shown that the channel does not extend through the absorbent core but merely within an inner region of the absorbent core 5.

Moreover, in FIG. 11c is the tension force 37 provided from the elastic threads of the first portion 45 schematically illustrated as two oppositely directed force arrows. This compression force 37 force in combination with the weakening feature 20 of the absorbent core is arranged to fold the absorbent core around the longitudinal direction to create a bowl shaped portion 36 within the absorbent core 5.

In FIGS. 12a and 12b are an alternative example embodiment of the weakening feature of the absorbent core disclosed. Here, three relatively narrow channels or slits form the weakening feature 20.

Still an alternative example embodiment of the weakening feature 20 of the absorbent core is disclosed in FIGS. 13a and 13b, which shown the weakening feature having also a certain transverse extension. The weakening feature may thus for example be embodied as two channels arranged perpendicular to each other and crossing in a centre thereof, such as to form a cross aligned with the longitudinal and transverse direction. Such a form of the weakening feature may be advantageous in formation of the bowl shaped portion. Here, three relatively narrow channels or slits form the weakening feature 20.

Still an alternative example embodiment of the weakening feature 20 of the absorbent core is disclosed in FIGS. 14a and 14b, which shows the weakening feature as a longitudinally extending channel having a V-shaped cross-section. The V-shaped cross-section may provide the required structural weakening of the absorbent core for enabling folding thereof in the front region whilst maintaining a larger amount of absorption capacity within the absorbent core 5.

Figure 15:
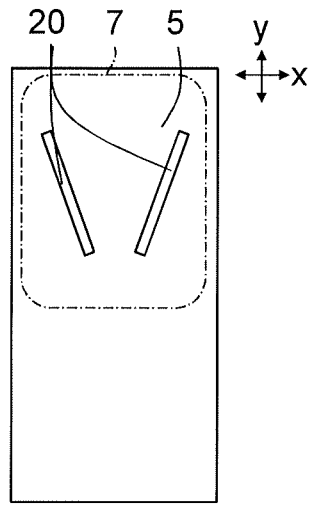
FIG. 15 shows yet a further example embodiment of the absorbent core according to the disclosure.

Still an alternative example embodiment of the weakening feature 20 of the absorbent core is disclosed in FIG. 15, which shows the weakening feature 20 as two substantially longitudinally extending channels, wherein each channel is slightly inclined with respect to a longitudinal direction y, such that a V-shaped weakening feature 20 is formed. This design of the weakening feature 20 may provide satisfactory results in terms of forming a bowl shaped portion in certain situations.

Figure 16:
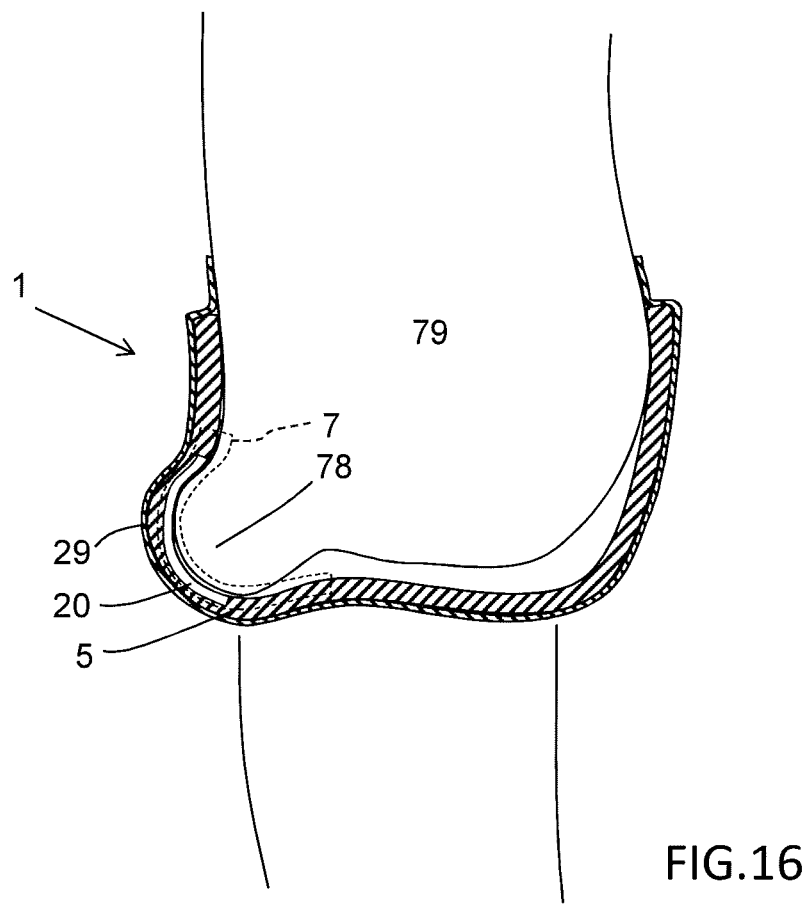
FIG. 16 shows a schematic cross-sectional view of an example embodiment of the absorbent core when being worn by a user.

FIG. 16 illustrates schematically an absorbent article according to the present disclosure when worn by a male user. The example embodiment of the absorbent article 1 comprises a weakening feature 20 in form of a longitudinally extending channel located in the front region 7. The side elastic elements 30 in combination with the specific arrangement of the elastic treads of the elastic web material of the present disclosure enables forming of a bowl shaped portion on the interior surface of the absorbent article 1 for receiving the genitals 78 of a male user 79. In the specific example embodiment of FIG. 16 the weakening feature 20 further improves forming of the bowl shaped portion. The absorbent article 1 of FIG. 16 is merely illustrated schematically with a back sheet 29 and an internal absorbent core 5.

A further embodiment of the invention relates to a laminated disposable pant-type absorbent article where an elastic layer is used to form an elastic material of the chassis. Further features of said embodiment may be accomplished by combining the various embodiments disclosed herein.

The present disclosure also includes a method for manufacturing a disposable pant-type absorbent article, such as a pant diaper, a sanitary pant or incontinence pant, in a continuous process, wherein a front region of the absorbent article is configured for receiving the genitals of a male user. The method may comprise a first step of forming a chassis from at least one continuous web material. The chassis has a front section and a back section, wherein the front section 3 at least partly is made of a laminated elastic web material comprising a plurality of elastic threads arranged in parallel with one another and extending in a substantially transverse x direction. A first portion of the plurality of elastic threads includes at least one elastic thread extending continuously over a central portion of the absorbent article for pressing a front portion of the absorbent core towards a user during use of the absorbent article, and a second portion of the plurality of elastic threads located more towards a back than the first portion includes at least one elastic thread extending on the transverse sides of the front region 7 but not completely over the front region 7 for enabling the absorbent core in the front region to bulge outwardly during use of the article.

The method may further comprise a step of providing the chassis with an absorbent core 5 and at least one elongated side elastic element attached in a substantially longitudinal direction on each transverse side 7a, 7b of the front region 7 for providing a side gathering effect along the transverse sides 7a, 7b of the front region 7. The side gather effect enables the absorbent core within the front region, under the influence of the side elastic elements and the laminated elastic web material to bulge outwardly during use of the article to form a bowl shaped portion for receiving the genitals of a male user.

In addition, the method may include manufacturing the laminated elastic web material of the front section 3 by attaching the plurality of elastic threads in a tensioned state between a first and a second sheet of web material while having the elastic threads configured to be located in a central portion 47 of the front section 3 of the finished absorbent article free from attachment to the first and second sheet of web material. The method subsequently includes interrupting the elastic threads located in the central portion 47 of the front section 3 of the finished absorbent article, such that the portion of the elastic threads located the central portion 47 of the front section 3 are allowed to return to their natural, un-tensioned, state.

The nonwoven material layers or webs 30, 31 of the present invention forming the chassis may for example be selected from, for example, of spunbond, air laid, wet laid, carded, electro spunned or meltblown nonwovens. The nonwoven material may be bonded by multiple techniques, e.g. by needling, hydroentangling, or heat bonding.

The nonwoven material of the disclosed products is a mixture of natural and synthetic materials. Natural fibres are for instance cellulosic fibres or fibres from regenerated cellulose.

The term "elastic thread" is intended to mean an elastic strand or elastic thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The threads may be of the elastane type that is available under the trade name "LYCRA", but any suitable elastic thread may be used. The threads may have a linear mass density, dtex, of about 80-1200 detex.

The elastic threads are elongated during the production process from about 50 to about 300% of the initial, non-tensioned original length, more preferably 100-250% and most preferably 150-220% of the initial, non-tensioned original length. The elastic threads should preferably be of a type that are able to tolerate an elongation of at least about 200% without breaking, so that they can be safely used in the production process without risk for breaking.

Further information with respect to material about the elastic web material is disclosed in WO2014098683 A1, which is referred to in its entirety.

The absorbent body may comprise any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like.

The absorbent body may have a liquid permeable topsheet placed on the side intended to face the skin of a user, and a liquid impermeable backsheet placed on the side of the absorbent body intended to face the garment of a user. Generally, the liquid permeable topsheet comprises or consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent body, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

An elastic band herein refers to member having a substantially flat cross-section.

The term "extended state of the absorbent core" used herein represents a state where the core is extended in a longitudinal direction y and transverse direction x until substantially all gathering of the core material caused by an attached elastic feature is eliminated, i.e. to a flat state of the core corresponding to a state before any elastic feature was attached thereto in a tensioned state to cause a gathering effect. The article is extended only to such an extent that this flat condition is reached. Similarly, the term "extended state of the chassis" used herein represents a state where the chassis is extended in a longitudinal direction y and transverse direction x until substantially all gathering of the chassis material caused by an attached elastic feature is eliminated, i.e. to a flat state of the chassis corresponding to a state before any elastic feature was attached thereto in a tensioned state to cause a gathering effect. The article is extended only to such an extent that this flat condition is reached.

The term male genitals refers to the penis and scrotum.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive.

The invention claimed is:

1. A disposable pant-type absorbent article comprising:
a chassis having a front section and a back section,
an absorbent core,
a front region configured for receiving genitals of a male user, and
a longitudinal direction and a transverse direction,
in which the front section at least partly is made of an elastic material comprising at least one elastic element,
wherein a first portion of the elastic material extends over at least a central portion of the absorbent article for pressing a front portion of the absorbent core towards a user during use of the absorbent article,
wherein a second portion of the elastic material is located more towards the back section than the first portion and includes at least one elongated side elastic element extending along each transverse side of at least part of the front region,
wherein the elongated side elastic elements are attached in a substantially longitudinal direction on each transverse side of the front region for providing a side gathering effect along each transverse side of the front region, such that the absorbent core within the front region, under the influence of the elongated side elastic elements and the first portion of the elastic material, is adapted to bulge outwardly during use of the article to form a bowl shaped portion for receiving the genitals of a male user.

2. The pant-type absorbent article according to claim 1, wherein the elongated side elastic elements extend along each transverse side of the core towards a crest of the core in the front section and end in a region between 70 mm below the crest of the core and 20 mm above the crest of core.

3. The pant-type absorbent article according to claim 1, wherein the first portion of the elastic material includes at least one elastic element extending over substantially the entire front section of the chassis.

4. The pant-type absorbent article according to claim 1, wherein at least one elastic element of the first portion of the elastic material is located either between the absorbent core and a waist elastic region, or between a thickest portion of the absorbent core and a front edge of the absorbent core, or positioned within a distance of 50 millimeters further down towards the back section as measured from the front edge of the absorbent core.

5. The pant-type absorbent article according to claim 1, wherein the first portion of the elastic material comprises a high tension zone compared with a longitudinally offset neighboring region of the first portion of the elastic material, wherein the high tension zone is located closer to the back section than the longitudinally offset neighboring region of the first portion.

6. The pant-type absorbent article according to claim 5, wherein elastic threads in the high tension zone have a higher elastic force than elastic threads in a longitudinally offset neighboring region of the first portion.

7. The pant-type absorbent article according to claim 5, wherein the high tension zone comprises 1 to 5 elastic threads.

8. The pant-type absorbent article according to claim 5, wherein the high tension zone is located along a front section of the front region.

9. The pant-type absorbent article claim 5, wherein the high tension zone comprises:
- at least one individual elastic thread having a higher modulus of elasticity than a neighboring elastic thread; and/or
- at least one individual elastic thread having a stronger pretension than a neighboring elastic thread; and/or
- a set of individual elastic threads having a smaller longitudinal separation from each other than a set of neighboring elastic threads.

10. The pant-type absorbent article according to claim 1, wherein a ratio of total mass of an absorption material between a front half of the absorbent core and a back half of the absorbent core in a longitudinal direction is at least 60/40.

11. The pant-type absorbent article according to claim 1, wherein the absorbent core comprises at least one weakening feature within the front region for reducing bending stiffness of the absorbent core within the front region.

12. The pant-type absorbent article according to claim 11, wherein said at least one weakening feature has an elongated extension arranged substantially in the longitudinal direction of the article for simplifying bulging of part of the absorbent core.

13. The pant-type absorbent article according to claim 11, wherein said at least one weakening feature has a longitudinal extension of about 3 to 20 centimeters, as measured in an extended state of the absorbent core.

14. The pant-type absorbent article according to claim 11, wherein a distance from a center of the weakening feature to a waist edge of the front section in the longitudinal direction is about 5 to 35 centimeters, as measured in an extended state of the absorbent core and chassis.

15. The pant-type absorbent article according to claim 11, wherein said at least one weakening feature of the absorbent core comprises:
- one or more elongated slits, channels, or compressions within the absorbent core, or
- a set of discrete slits, channels or compressions arranged along a substantially straight line within the absorbent core.

16. The pant-type absorbent article according to claim 11, wherein the absorbent core, as seen in a thickness direction of the core, comprises an inner region that is adapted to face a user and an outer region that is adapted to face the garment of user, and the weakening feature is located in the inner region of the absorbent core.

17. The pant-type absorbent article according to claim 11, wherein the absorbent core comprises at least two layers located on top of each other, and the weakening feature is provided in an inner layer of the two layers.

18. The pant-type absorbent article according to claim 17, wherein the outer layer is free from a weakening feature within the front region.

19. The pant-type absorbent article according to claim 1, wherein the elongated side elastic elements extends backwards in the longitudinal direction along the transverse sides of the absorbent core to form leg elastic members along the periphery of the leg openings in a crotch section of the absorbent article.

20. The pant-type absorbent article according to claim 1, wherein the web material of the chassis is substantially free from any tensioned elastics at a central portion of the front section.

21. The pant-type absorbent article according to claim 20, wherein the central portion of the front section has a substantially square shape with an area in the range of 20-150 square centimeters.

22. The pant-type absorbent article according to claim 20, wherein the elastic element of the central portion of the front section has been interrupted and are not attached to any sheet of web material of the laminated elastic web material within the central portion.

23. The pant-type absorbent article according to claim 1, wherein each of the front and back sections of the chassis comprises a waist edge, a pair of side edges and a pair of leg edges, wherein the front and back sections are joined to each other by means of a pair of side connections, each side connection extending along two opposite side edges to at least partly define a waist-opening and a pair of leg-openings.

24. A method for manufacturing a disposable pant-type absorbent article, wherein a front region of the absorbent article is configured for receiving genitals of a male user, the method comprising:
- forming a chassis from at least one web material, the chassis has a front section and a back section, wherein the front section at least partly is made of an elastic web material comprising at least one elastic element, wherein a first portion of the elastic material extends over at least a central portion of the absorbent article for pressing a front portion of the absorbent core towards a user during use of the absorbent article, and wherein a second portion of the elastic material is located more towards a back than the first portion and includes at least one elongated side elastic element extending along each transverse side of at least part of the front region; and
- providing the chassis with an absorbent core, wherein the elongated side elastic elements are attached in a substantially longitudinal direction on each transverse side of the front region for providing a side gathering effect along each transverse side of the front region, such that the absorbent core within the front region, under the influence of the side elastic elements and the laminated elastic web material is adapted to bulge outwardly during use of the article to form a bowl shaped portion for receiving the genitals of a male user.

25. A method for manufacturing the disposable pant-type absorbent article according to claim 24, further comprising providing the elongated side elastic elements along each transverse side of the core towards a crest of the core in the front section and ends in the region between 70 mm below the crest of the core and 20 mm above the crest of core.

26. The method according to claim 24, further comprising:
- manufacturing the laminated elastic web material of the front section by attaching a plurality of elastic threads in a tensioned state between a first and a second sheet of web material while having the elastic threads configured to be located in a central portion of the front section of the finished absorbent article free from attachment to the first and second sheet of web material; and interrupting the elastic threads located in the central portion of the front section of the finished absorbent article, such that the portion of the elastic threads located the central portion of the front section are allowed to return to their natural, un-tensioned, state.

* * * * *